United States Patent [19]
Kempen

[11] Patent Number: 5,435,448
[45] Date of Patent: Jul. 25, 1995

[54] INTRAVENOUS WORKSTATION AS A MEDICAL TOOL ORGANIZING DEVICE

[75] Inventor: Paul M. Kempen, Adrian, Mich.

[73] Assignee: Paul Martin Kempen, Shreveport, La.

[21] Appl. No.: 222,446

[22] Filed: Apr. 4, 1994

Related U.S. Application Data

[63] Continuation-in-part of Ser. No. 976,880, Nov. 16, 1992, abandoned.

[51] Int. Cl.[6] .................................................. A61B 19/00
[52] U.S. Cl. .................................... 206/370; 206/364; 211/70.6
[58] Field of Search ............... 211/70.6, 107; 206/363, 206/370, 364, 562, 561

[56] References Cited

U.S. PATENT DOCUMENTS

| | | | |
|---|---|---|---|
| 3,776,387 | 12/1973 | Brent | 211/70.6 |
| 3,920,295 | 11/1975 | Spechin | 211/107 X |
| 4,583,647 | 4/1986 | Schinzing | 211/70.6 X |
| 4,844,249 | 7/1989 | Coulombe | 206/370 X |
| 5,099,912 | 3/1992 | Heimreid | 206/370 X |

Primary Examiner—Jacob K. Ackun, Jr.

[57] ABSTRACT

A medical intravenous workstation comprises a rigid plate adapted to be clamped to a pole. The plate comprises bores, slots and other structure for holding Y-ports, hypodermic syringes, and other equipment used by an anesthetist.

7 Claims, 2 Drawing Sheets

INTRAVENOUS WORKSTATION AS A MEDICAL TOOL ORGANIZING DEVICE

This application is a continuation-in-part of U.S. application Ser. No. 07/976,880, filed on Nov. 16, 1992, and now abandoned.

BACKGROUND OF THE INVENTION

1. Field of the Invention

This invention relates to the field of medical equipment, and more particularly to a device, which can hold any and all components involved in the insertion of an intravenous cannula into a patient's vein and allow the subsequent administration of drugs or fluids into an intravenous administration set, whereby the risks and associated dangers of health care worker laceration and needle stick injury during the recapping of hypodermic or cannulae needles, the opening of ampules or administration of drugs from syringes, directly or via hypodermic needle into intravenous tubing, are eliminated by enabling a single handed process.

2. Description of the Prior Art

The prior art teaches a variety of storage racks, storage trays, and organizing devices which facilitate neat, convenient storage and holding containers for various medical devices, needle syringe assemblies and other medical and non-medical tools. The prior art addresses the need for providing convenient access to the equipment during a medical procedure. The prior art also addresses a device which carries needles in such a manner, that the medical personnel are spatially protected from directly contacting the needle itself, and therefore, reducing the possibility of being punctured with a contaminated needle during a medical procedure, as a contaminated needle may carry a contagious disease, such as the AIDS virus.

Examples of the prior art are found in U.S. Pat. Nos. 2,659,485, 2,974,804, 4,023,757, 4,049,126, 4,411,868, 4,658,957, 4,844,249, 4,846,803, 4,875,583, 4,911,083, 4,921,199, 4,951,685, 4,966,582, 4,973,315, 5,069,666, 5,156,426 and 5,099,992. The prior art describes different variations of utility trays and or containers, which have needle and/or syringe holders and may have other compartments for storing and/or transporting a plurality of used and/or unused syringes, alcohol wipes, and/or vials of medication, and the like. Most of these devices of the prior art deal with needles and the danger of needlestick injury only in regard to the recapping process of the contaminated needle and after completion of a singular injection or blood withdrawal using one syringe-needle assembly. Among these devices is the medical supplies container, subject of U.S. Pat. No. 4,844,249 granted to Coulombe et Al., which is a hand-held transport container and can provide for physical separation of a restraining hand from the needle cap during recapping, reducing the danger of needlestick.

Further is the Needle Guard, subject of U.S. Pat. No. 5,156,426 granted to Graves, which is a hand held instrument with holes to accommodate syringe caps and slots to accept Y-ports, having a design to allow the injection from a singular syringe into only latex ports of the Y-port type. Similarly, Sit et Al. describe in U.S. Pat. No. 4,966,582 a device which will accept only ports of the latex Y-port type and allow injections from syringes and recapping to occur using two hands. Another device as described by Gericke in U.S. Pat. No 5,069,666 also allows for the restraint of a port of the latex Y-port type only, within a hand held device, which allows the bimanual insertion of a singular syringe-needle unit into the port and recapping of the needle to occur with only a relative degree of protection from needlestick injury. It will further alternately restrain and secure in place up to three secondary intravenous tubings within the latex port.

Villaveces describes a device in U.S. Pat. No. 4,921,199 which serves to restrain a transcutaneous cannula for intravenous placement by its protective cap and in a fashion to allow single handed removal of the unit from the cap. There is also a small c-clamp appendage to hold the end of the intravenous tubing in ready for connection to the cannula after the cannula has been inserted into the patient's vein. An associated disposable styrofoam block is described, which serves to receive the needle after placement of the plastic cannula into the vein, so as to facilitate subsequent connection of the intravenous tubing to the cannula and fixation to the patient.

Heimried describes a device in U.S. Pat. No. 5,099,992, which organizes syringes containing drugs with the associated and respective drug vials on a common block to provide sterile restraint of syringes without needles for convenient and aseptic use. While all of these examples of prior art provide some manner of protection and/or benefit to the user in situations of very narrow scope, they fail to comprehensively address the multiple and very critical issues pertinent to intravenous therapy in the setting of anesthesia in the 1990's: Foremost, needlesticks occur because the opposing hand is placed in front of the needle and because considerable force is often required to pierce a latex membrane. Needles remain an integral component in intravenous drug administration. During anesthesia, multiple injections should be completed and preferably using one hand only, to effectively eliminate and not simply reduce needlestick risk, as well as to allow for simultaneous and continuous maintenance of the patient's airway during injections. It is also necessary to maintain strict asepsis of all intravenous components over a period of hours, as typically numerous incremental doses of drugs from the multiple syringes are administered to meet the patient's needs as they occur throughout the anesthetic. There is a need to organize a multiplicity of syringes of different types and manufacture, aseptically near the patient, the anesthetist and together with the injection ports in a manner to accommodate the needle and sheath assemblies of all types and sources of manufacture on a completely reusable device.

The introduction of hooded needles into medical practice requires that the latex ports be restrained by a device in a fashion to allow free access to the whole circumference of the latex membrane of the Y-port. This will allow entry with hooded needles, while providing protection from standard hypodermic needles and, at the same time, the port need not be removed from the protective device, when such hooded needles are utilized for injections. The close proximity of the aseptic latex port membrane to the restraining surfaces themselves contribute to needle contamination and this proximity should be avoided. Only one hand should be utilized throughout the injection process to eliminate exposure of an opposing hand to unsheathed needles. A reusable device should maintain aseptic surfaces of intravenous therapy components distant from non-sterile surfaces of the device itself, to prevent contamination of aseptic surfaces which are positioned and reused during anesthesia. Such a design will allow the device to be utilized and reused while observing only standard aseptic techniques. Safety devices are avoided when associated user inconvenience results. The device should simplify the procedure and be easy to use to ensure high user compliance.

It is the object of the present invention to provide a work area which will restrain, fixed in space, all and any intravenous components in common use, in a generic fashion being independent of type or manufacture. Needles, syringes, injection ports, sharp ampule fragments, intravenous tubings and transcutaneous cannulae are restrained by the external and typically contaminated surfaces of the ports, tubings or needle caps, as to allow single handed fracture of ampules, drug injection and recapping of needles in a safe and aseptic fashion. Because only one hand is used and remains behind the needle at all times, the possibility of needlestick injury is effectively eliminated and not merely reduced, as would occur by merely placing the opposing hand at a distance from the exposed needles as per prior art methodologies. This single handed technique will allow simultaneous control of the patient airway during the injection process and facilitate insertion of transcutaneous cannulae. The device will be reusable in its entirety, durable and readily mounted onto any intravenous pole at a height and location convenient to the anesthetist and will function without requiring the utilization of any additional or special disposable items. It will restrain tubings and needles in a state of readiness for insertion into the vein or during use thereafter, will allow ampules to be opened using a single hand and without laceration injury and will further facilitate the maintenance of aseptic surfaces in an aseptic state. Ports will be restrained to allow syringes or secondary infusions to remained connected directly or via needle, without danger of these syringes or infusions becoming displaced or leading to their contamination or puncture of attending personnel's skin.

Above all, the use of such a device must allow compliance with the requirements of the Occupational Safety and Health Administration's safety guidelines for health care professionals, without creating significant new difficulties for the user. The device must be simple to use/understand and require little or no training to use effectively/safely. The device should reduce work and increase safety regarding the completion of I.V. injections, and particularly those injections utilizing needles, into intravenous tubing and injection ports of any and all types and from any manufacturer. As a device designed for the setting of anesthesia, there remains a need for a device which, in a generic fashion accepts all commonly encountered intravenous paraphernalia, organizes multiple drug filled syringes together with an adequate number of injection ports, facilitates multiple injections and allows them to occur serially and with only one hand. The reusable device should mount easily and securely for use onto intravenous poles commonly used to suspend intravenous solutions and to provide continuous availability in the operating room, while allowing for convenient removal for cleaning, should gross contamination occur.

SUMMARY OF THE INVENTION

The present invention has met all of the above described needs and is a planar device which is readily mounted parallel to the floor onto any conventional Intravenous pole via an integrated clamping mechanism. It will restrain multiple needle sheaths of all sizes perpendicular to the earth's surface within tightly fitting apertures, which provide secure restraint and organization of multiple needles and any connected syringes within the work area. The design further additionally utilizes gravity to contribute to the restraint of all components within the workstation. Using one hand only, specific apertures receive the upper portion of glass ampules to allow ampule fracture and drug removal eliminating hand lacerations, which frequently occur when two hands are used to fracture open glass ampules. Multiple apertures are provided to allow for secure restraint and organization of injection ports of any type and, with the associated and adjacent cylindrical surfaces and slots, provide a positive locking mechanism by utilizing the adjacent flexible tubing to hold the ports and tubings in place, maintaining aseptic surfaces distant from non-aseptic surfaces during use. All latex ports are secured in a fashion to maximally expose the aseptic latex membranes for needle insertion, so as to allow penetration with hypodermic or hooded needles, while restrained on the device. A separate fixture is present to restrain Y-ports of any common configuration by directly accepting their rigid bodies and in the absence of immediately adjacent flexible tubings to provide fixation. With needle caps and ports fixed spatially, the syringes can be moved, with or without needles, from one site to the other using only one hand to complete all injections and without any danger of needle injury.

DETAILED DESCRIPTION OF THE DRAWINGS

Figure 1:
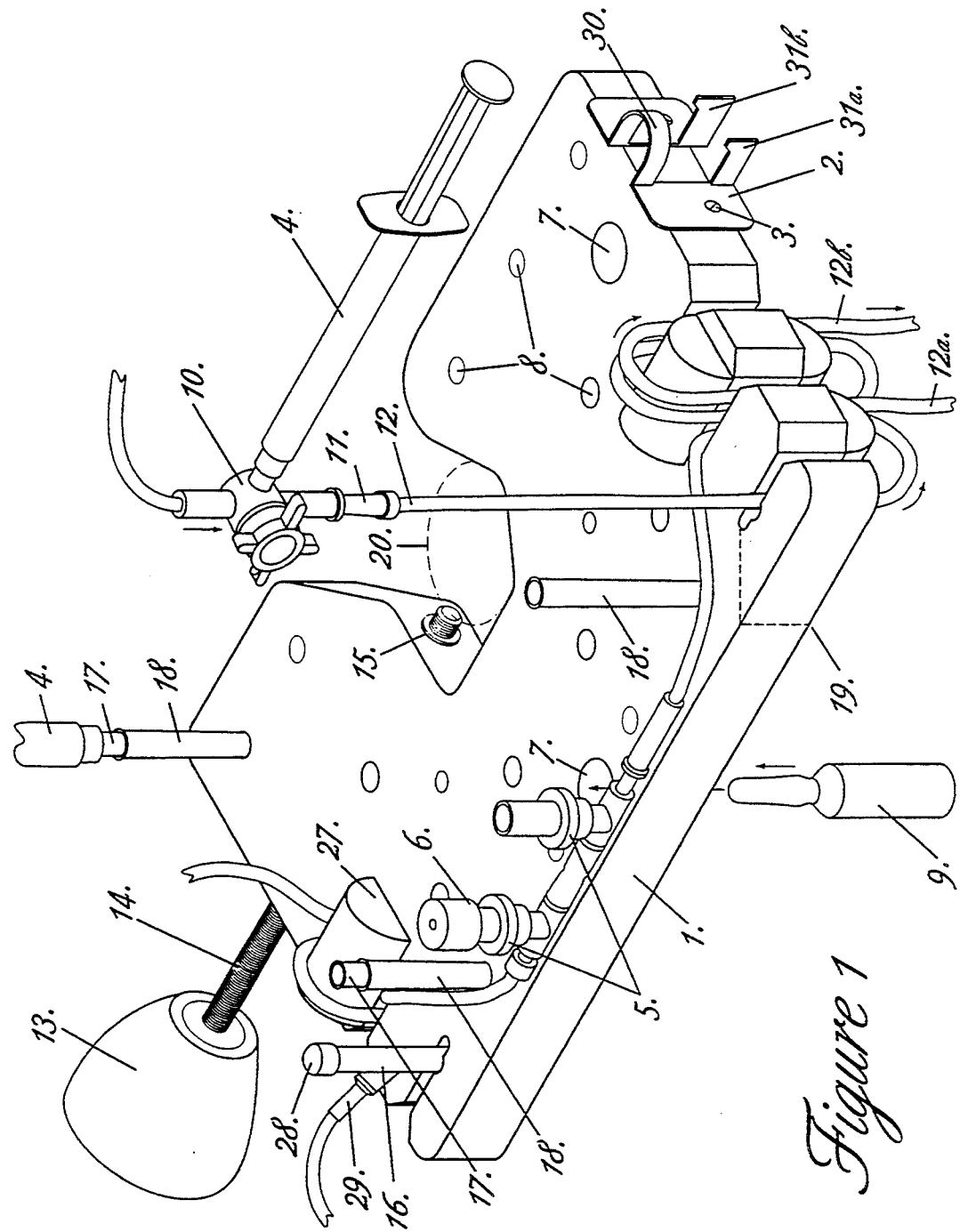
FIG. 1 is a perspective view of the present invention in it's entirety and with multiple typical medical devices mounted in place.
Figure 2:
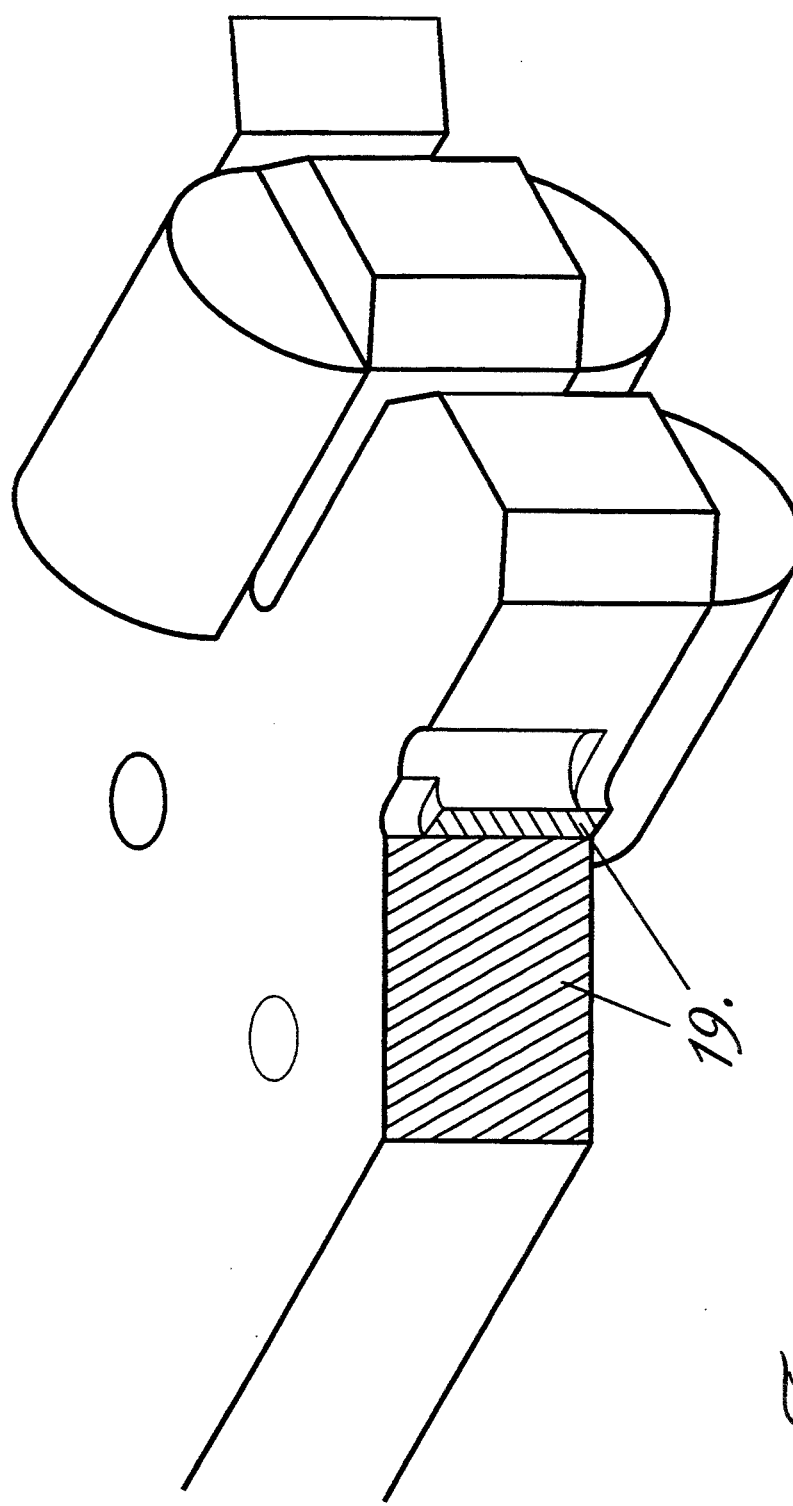
FIG. 2 is an enlargement of the right front corner of the device only and with a portion cut away as indicated in FIG. 1 to allow view of the internal geometry and facilitate recognition of the port restraint surfaces.

Referring to the drawings, in FIG. 1 is shown a perspective drawing of the complete intravenous workstation with multiple common medical devices. In FIG. 2, the geometry of the port restraint is clearly shown with the anterior portion of the plate removed along the planes 19 indicated by the dotted line in FIG. 1. The workstation is a ¾ to 1 inch thick plate 1 of rectangular shape, with a centrally located aperture to the rear 20, which will accommodate the insertion of a cylindrical intravenous pole of up to 1.5 inches diameter. Six segments of half-cylindrical rods 27 are strategically affixed on the upper and lower surfaces as shown. A knob 13 is used to move a threaded shaft 14 within the threaded bore of a fastener 15 to clamp against an intravenous pole within this clamping mechanism aperture 20, allowing the invention to be secured on a cylindrical intravenous pole at the desired height.

Within the interior of the plate 1 are located multiple bores 8, having diameters which allow the insertion and firm compressive restraint of commercial needle or cannulae sheaths 18 by their exterior surface. Commercial needle and cannulae sheaths are typically slightly conical in shape, due to the nature of the injection molding process, and allow for firm restraint by the bores upon initial insertion of the most distal tip only and develop increasingly secure restraint as they are inserted deeper into the bore. The bores 7, 8 are placed perpendicular to the plate surface, are arranged in rows to allow rapid recognition of the appropriate diameters and are spaced to maximally distance each bore from the adjacent bores within the confines of the area of the plate 1. After insertion of the sheath 18, needles 17 and the associated syringes 4 are organized and restrained to allow single handed removal, injection and return to the sheath or port during the drug administration process, as all other components 18, 5, 16, 10 are restrained and secured in space by the Plate 1. The needle 17 is restrained by the sheath 18 to allow removal of the syringe 4 without the needle via a rotational motion, should Leur ports 5, 10 be utilized for injection. Similarly, cannulae sheaths 18 are restrained to allow single handed cannula removal and needle reinsertion into the sheath during transcutaneous cannula insertion into the patient's vein. Intravenous tubings can be held ready for connection to the sited cannula by inserting them into the tubing slots 26 as described below.

Near the front surface on each lateral edge is a port restraint 22, which opens to the nearest lateral edge via a tubing slot 23. This tubing slot extends into the body of the plate 1 to end within the cylinder of the port restraint 22, except for along the superior surface, where it 21 continues linearly past the port restraint about 1.5–2 tubing widths and to a similar depth from the superior surface. This has been done to ensure that tubing 12, used to secure multiple Luer ports 5 along the anterior edge of the plate 1 and in the two port restraint apertures 22, will not kink as the tubing bends 90° as the direction changes from coaxial to the cylinder of the port restraint aperture 22 to parallel to the upper surface of the plate 1. The cylindrical shape of the tubing 12 is maintained within this tight fitting slot 21 as described below for the medial end of the tubing slots 26.

On each lateral edge of the plate 1 are located two tubing slots 26 into which lengths of intravenous tubing 12 have been introduced. The slots 26 are widened 25 as they begin to merge with the lateral surface of the plate 1, to facilitate insertion of tubing 12 into the slots 26. The medial end of the slots 26 are rounded with a radius only slightly less than that of the intravenous tubing 12. This rounded end of the slot 26 insures that any tubing which is secured between two slots located on contralateral sides of the plate 1, as is the tubing connected to the serial Luer ports 5 shown, remains cylindrical at this point and will not flatten or kink upon the superior edge as the tubing emerges from the tubing slot 26 and becomes parallel to the upper surface of the plate 1. In this manner, the effective lumen of the tubing remains patent and fluid flow within the tubing 12 is not compromised. The slots 26 extend a sufficient distance from the edge of the plate to accommodate multiple lengths of tubing 12a, 12b to lay side by side within the slot 26 as they pass from the superior to the inferior surfaces. The width or distance between the parallel walls of each tubing slot 26 is such that the diameter of the inserted tubing 12 is slightly greater, which insures substantial friction between the external surfaces of the tubing 12 and the parallel walls of each slot 26 and without significantly compromising the lumen of the tubing.

Located on each upper and lower surface of the plate 1 and between each pair of tubing slots 26, sections of half-cylindrical rod 27 are permanently affixed, such that the longitudinal edges of each length of rod 27 are exactly aligned with the edges of both adjacent tubing slots. This geometry provides a smooth transition from the parallel wall of the tubing slot and the surface of the half-cylindrical rod 27. The tubing 12 follows the curve of the half-cylindrical rod 27 without kinking as it emerges from one slot to enter the adjacent tubing slot, while changing direction 180°. The rounded surfaces of these rods 27 also provide surface friction against the tubings 12 as they lay in place and prevent coaxial movement during port 5, 10, 16 use. These half-cylindrical rods 27 extend from the point where the tubing slot walls become parallel, to well past the medial end of the tubing slots. The inferior aperture 23, 24 of the port restraint 22 has the same geometry as all tubing slots at the point of merger with the inferior surface of the plate 1. Similarly, a section of half-cylindrical rod 27 is located on the inferior surface between the tubing slot 23, 24 of the port restraint 22 and the adjacent tubing slot 26.

The port restraint 22 is a cylindrical sleeve into which the larger diameter hard plastic cylindrical portions of Leur connections 11 of singular injection ports 10, or the bodies of Y-ports 16 can be introduced and effectively restrained after introducing the connected pliable tubing 12, via the tubing slot 23–24, which opens to the lateral edge of the plate 1. The wider cylindrical bore of the port restraint 22 does not go completely through to the lower surface, as the narrower tubing slot 24 allows only the thinner pliable tubing 12 to exit. This design retains the hard plastic appendages of the port 11, 16 above the lower surface of the plate, so as to allow the pliable tubing 12 to exit smoothly and without kinking to follow the surface of the cylindrical rod 27 as it passes around to the adjacent tubing slot 26. This design also limits the distance that the rigid plastic portions of ports can enter this restraint, maintaining the sterile surfaces significantly above the surface of the device, to thus facilitate asepsis during port use. With a singular injection port 10, 16 above the upper surface of the plate 1, the adjacent and pliable tubing 12 is pulled through the slot 23 and, with the tubing placed coaxially within the cylindrical port restraint 22 and terminal end of the inferior tubing slot 24, the hard plastic portion of the tubing 11 or body of the Y-port 16 is pulled down and seated into the port restraint 22. The Y-port is shown seated in place, while the stopcock's 10 Leur connector 11 must be pulled into place by the tubing 12b as shown in FIG. 1. The pliable tubing 12 is now placed into one or more nearby slots 26 and over the cylindrical rods 27 as shown and then pulled firmly downward by the free end, as indicated by the arrows along the tubing 12b connected to the stopcock 10 in FIG. 1, to secure the port within the restraint 22 and against upward motion, which could dislocate the port 10, 16 from the restraint 22 during use.

Similarly, when multiple Luer ports 5 are connected in series, they can be restrained across the upper surface of the plate with each end of the pliable tubing restrained in tubing slots on each contralateral edge of the plate, as demonstrated with the darker tubing 12a. These multiple ports 5 are automatically restrained along the front edge of the plate, when held between the two port restraints 22, or can be placed in this preferred position, should the port restraints be otherwise occupied, by inserting two needle caps 18 into the anterior apertures 8 and passing the two tubing ends 12a anteriorly to these needle caps before securing them in contralateral tubing slots 26 as shown in FIG. 1.

In FIG. 2 the geometry of the surfaces 21, 23, 24, 25 around the port restraint 22 is clearly shown with the anterior wall of the plate removed along the planes 19 as indicated in FIG. 1. The superficial end 21 of the tubing slot 23 continues past this port restraint sleeve 22 on the upper surface of the plate to a depth and length of 1.5 to 2 tubing 12 widths only. The length of the tubing slot 23 of the port restraint 22 is sufficient to allow the pliable tubing connected to the side arm 29 of any Y-port 16 to be pulled downward and restrained within this tubing slot and to cause occlusion of the tubing at this junction to the hard plastic of the Y-port arm. In this way, the occluded tubing prohibits retrograde flow from the Y-port, when single handed injections are made into tubings without mechanisms to prevent retrograde flow of fluids during injections.

As latex Y-ports occur on commercial tubings without significant sections of flexible tubing connected to the downstream end of the port, an additional restraint 2 is provided and affixed to the plate 1 by screws 3 to allow insertion and effective restraint of Y-ports by the rigid body 16 and side arm 29 of the port and with circumferential exposure of the latex membrane 28. As Y-ports have variable thickness and geometry, the additional restraint 2 has two inferior support arms 31a, 31b separated from the superior hoop 30 by differing distances, which allow for firm restraint of all Y-ports exhibiting any extreme of typical geometric shape. The Y-port latex membrane 28 is introduced from below between the support arms 31 and upward through the hoop 30 to place the Y-port body 16 laying against the plate 1 and the side arm 29 of the Y-port impinging against the inferior edge of the hoop 30. The side arm 29 of the port is then rotated 90° to the right or left to then lay parallel to the plane of the edge of plate 1, between the hoop 30 and either support arm 31a or 31b, as is appropriate for firm restraint of the port relative to the specific diameter of any given Y-port side arm. The force of needle entry and removal are coaxial to the cylinder of the Y-port body 16 and is counteracted by the side arm 29 impingement against the side arm 31 or hoop 30.

The narrow and superior portion of any ampule 9 can be fully inserted into the larger diameter apertures 7 from below, as indicated by the arrow in FIG. 1. Using one hand to hold the larger body of the ampule and resting against the plate 1, the isthmus portion of the ampule can be safely fractured without laceration or overshoot movements, when rotational torque against the restrained upper portion is applied. The upper portion of the ampule typically moves upward at the moment of fracture and moves freely within the aperture to then fall per gravity into the waiting hand. Hand laceration typically results during bimanual opening, as sudden and uncontrolled motion occurs at the moment of fracture, causing both hands to suddenly move past each other with firmly restrained and sharp ampule fragments. The narrow upper portion will alternately completely shatter to result in direct laceration. Both mechanisms of injury are eliminated with the device.

While a specific embodiment of the invention has been shown and described, it is to be understood that numerous changes and modifications may be made therein without departing from the scope and spirit of the invention as set forth in the appended claims. Particularly, the means to affix this device to appropriate surfaces other than a cylindrical pole are recognized and possible with appropriate modification or the addition of appropriate accessories.

I claim:

1. A rigid medical intravenous workstation, which alone is capable of restraining, organizing and immobilizing, at a location convenient to the anesthetist and in a manner to eliminate user infection or injuries from needles or glass ampule fragments, while facilitating and enabling single handed opening of vials, single handed aseptic serial connection and removal of multiple syringe bodies, directly or via needles, to and from restrained injection ports and needle sheaths, as well as single handed retrieval of transcutaneous cannulae and resheathing of the used cannula needle after cannula placement, the following: the upper end of glass ampules; intravenous injection ports and connected tubings of any type including latex Y-ports, latex flash bulbs, singular or serially connected stopcocks or Leur locking ports; multiple hypodermic syringe members having a rigid body part, a permanently affixed or removable needle and needle sheath; one or more intravenous cannula members having a sheath, a plastic cannula and a needle; and comprising:
    a) a rigid plate constituting a work area of generally rectangular shape of around 45 square inches, said plate having a thickness up to one inch, bluntly rounded corners and edges, with generally planer and parallel upper and lower surfaces made of plastic or metal, with generally parallel lateral edges being separated by a distance greater than the length of 4 serially connected stopcocks, with each lateral edge having multiple lengths of half-cylindrical rod affixed to the superior and inferior surfaces at right angles to the lateral edges and between parallel tubing slots extending inwardly of the plate from the edges thereof;
    b) a Connection means allowing the introduction of a cylindrical upright intravenous pole from an edge of the plate into a central portion of the work area, and enabling spatial fixation of the plate and all restrained medical equipment upon said pole;
    c) a plurality of aperture means in said plate of adequate diameter to receive, mildly compress and simultaneously frictionally secure multiple needle and/or cannulae sheaths, to allow single handed removal from and replacement of needles to their respective sheaths, or syringes onto their respective needles, which are in turn restrained in their respective sheaths by said aperture means;
    d) a plurality of bores in said plate of a diameter sufficient to restrain the narrow tubular portions of glass ampules during the application of rotational torque upon the narrow isthmus of the ampule, in order to effect fracture of the ampule at the isthmus, utilizing only one hand and in a manner to exclude hand laceration;
    e) a plurality of tubing restraints of adequate diameter for quickly receiving, compressing and frictionally holding pliable intravenous tubings in place, said tubing restraints comprising a plurality of slots on exposed lateral edges of said plate, said slots extending inwardly towards the central portion thereof such as to eliminate significant lateral or coaxial movement of the tubing and without significant compromise of fluid flow through the tubing while restrained, particularly as the tubing passes from slot to slot over curved surfaces formed by said multiple lengths of half cylindrical rod;
    f) a plurality of injection port restraints of specific diameter and dimensions for quickly receiving and coaxially restraining, in conjunction with ones of the said tubing restraints, hard plastic cylindrical portions or appendages of singular commonplace injection ports of any type or manufacture, or maintaining the tubing of serially connected Leur ports along the anterior edge and superior surface of said plate and between two such injection port restraints, so as to maintain the sterile surfaces of the ports immobile and significantly distant from the surface of the plate and thus allow the connection of syringes, directly or via hooded or hypodermic needle as appropriate, and enable drug administration into the intravenous line using only one hand said injection port restraints comprising cylindrical sleeves coextensive with said slots, and extending generally perpendicularly to said slots while being spaced from ends thereof; and g) a singular Y-port restraint comprising a hoop, said restraint attached to an edge of said plate for quickly receiving and restraining Y-ports of any make or manufacture by their hard plastic body and side arm and to thus allow injections using one hand only and without danger of needle stick injury to the user.

2. A medical intravenous workstation as defined in claim 1 comprising:
 a) said connection means forming a clamp including a symmetric V shaped surface within the body of the plate, which opens directly toward a threaded hand engageable tightening member located opposite the point of angulation of the V shaped surface, the planes of this surface connecting and being perpendicularly oriented to the superior and inferior surface of the plate and which is accessible to a cylindrical intravenous pole through a wide aperture in the rear of the plate; and
 b) a channel within the plate having threaded fasteners on each end and a threaded hand engageable tightening member for threadable receipt therein, with said channel within the plate and having an axis parallel to the plate's upper surface and front edge and being directed perpendicularly onto the point of angulation of the V shaped surface from the opposite side of the wide aperture, such that it can be brought to tightly compress the said cylindrical and upright intravenous pole between the tightening member and the V shaped surface, that the plate is fixed in space parallel to the earth's surface, perpendicular to the cylinder axis of the pole and upon the intravenous pole.

3. A medical intravenous workstation as described in claim 1, wherein the multiple aperture means are of specific diameters made slightly less than the mean diameters of various commercial needle sheaths, so as to provide compressive friction onto said sheaths upon their insertion and with increasing friction as sheaths are increasingly inserted, have rough internal surfaces to encourage friction, are spaced 1-2 inches apart, are organized in rows and color coded to facilitate recognition the diameter of each cylindrical aperture to allow matching to respective diameter needle sheaths and which pass completely through the plate at a 90° angle to insure that gravitational forces contribute to the immobilization of needles within restrained sheaths, when the device is mounted.

4. A medical intravenous workstation as described in claim 1, having at least one or more cylindrical bores passing completely through the plate and having sufficient diameter to allow the insertion of the upper end of any common glass ampule from below the plate surface without resistance and, while holding the ampule body in one hand only and biasing it away from the axis of said bore, the ampule can be fractured at the isthmus located between this upper portion of the ampule and the ampule body containing the drug, causing the ampule to be opened without a danger of hand laceration from the fractured surfaces or spillage of contained drug.

5. A medical intravenous workstation as defined in claim 1 comprising:
 a) said tubing restraints consisting of slots arranged parallel to each other, whereby the side walls are perpendicular to the superior and inferior surfaces of the plate, are parallel to each other, are separated by a distance slightly less than the width of the intravenous tubing and extend from the lateral edge of the plate into the body of the plate a distance of sufficient length to enable multiple segments of tubing to lay in the slot side by side, with each slot's medial end terminating in a cylindrical shape of a radius equal to one half the width of the slot, while widening at the lateral end to join the lateral surface of the plate and thus to facilitate the insertion of tubing into the slots; and
 b) sections of said half-cylindrical rods, which extend slightly further medially than the tubing slots, are positioned on the superior and inferior surfaces between each pair of tubing slots, such that the edge of each rod is aligned exactly with the parallel edges of each tubing slot on each side, to allow tubing to follow the curvature of the rod without kinking, while incurring significant friction against slippage, as the tubing passes from slot to adjacent slot over the surface of the rod.

6. A medical intravenous workstation as defined in claim 1 comprising:
 a) said injection port restraints having a cylindrical bore of a diameter just greater than that of the hard plastic body of Y-ports, Leur port appendages or tubing connectors, which is perpendicular to the surface of the plate and penetrates into the plate from the superior surface only through ¾th of the total plate thickness, thus creating an upright sleeve for restraint of non-pliable singular ports or port appendages and without passing through the inferior surface of the plate and in a manner that the sterile surfaces of the ports remain significantly above the superior surface of the plate; and
 b) a tubing slot of length and dimensions similar to those described in claim 5, which extends into the cylindrical bore from the lateral edge of the plate as well as into the inferior surface below the terminal inferior end of the cylindrical bore, that pliable tubing may be admitted from the lateral edge coaxially into the bore and completely through the plate, that the connected, larger diameter hard plastic port components may be then introduced into the cylindrical bore from above to be coaxially restrained within said cylindrical bore superior to the inferior surface of the plate and without friction against rotation within the cylinder; and
 c) an extension of the tubing slot along the upper surface, which reaches 1.5-two tubing widths deep into the plate from the superior surface and continues a similar distance medially past the cylindrical bore; and d) a section of half cylindrical rod, which is longer than the tubing slots, is affixed to the inferior surface such that the edge of the rod is aligned exactly with the edge of the said tubing slot of the port restraint and the edge of the tubing slot located posterior, adjacent and parallel to the tubing slot of the port restraint, to allow pliable tubing to follow this curvature of the rod without kinking while incurring significant friction against slippage as it passes from slot to adjacent slot over the surface of the rod.

7. A medical intravenous workstation as defined in claim 1 comprising:
   a) said singular Y-port restraint, which has two planer mounting members which affix onto the lateral surface of the plate with screws and has said cylindrical hoop connecting both planar mounting members at their superior ends; and
   b) said hoop is of sufficient diameter and minimal height to allow any commercial latex Y-port membrane portion to pass through it from below and to enable restraint of the latex injection site, while allowing circumferential exposure of the latex membrane above the upper rim of the hoop; and
   c) exhibits two upright planar support arms, each extending perpendicularly away at the inferior medial edge of the planar mounting member, at two different distances below the hoop as measured along the medial edge of each planar mounting member, that Y-ports of all geometry can be snugly restrained against their side arms with the latex membrane maximally elevated above the hoop and with the side arm of the Y-port resting snugly between a support arm and the hoop; and
   d) having slightly elevated prongs on the terminal $\frac{1}{4}$th length of the superior surface of each support arm, to prevent movement of the side arm of the Y-port over the free end of the support arm, while restrained.

* * * * *